(12) United States Patent
Berrang et al.

(10) Patent No.: US 6,306,168 B1
(45) Date of Patent: Oct. 23, 2001

(54) MEANS FOR IMPLANTING A DEVICE IN THE CANALIS COCHLEARIS

(75) Inventors: Peter Berrang; Alan Lupin, both of Victoria (CA)

(73) Assignee: Epic Biosonics Inc., Victoria (CA)

( * ) Notice: Subject to any disclaimer, the term of this patent is extended or adjusted under 35 U.S.C. 154(b) by 0 days.

(21) Appl. No.: 09/070,999

(22) Filed: May 4, 1998

(51) Int. Cl.⁷ .................................. A61F 2/18; A61N 1/00
(52) U.S. Cl. .............................................. 623/10; 607/137
(58) Field of Search ............................. 623/10; 607/137, 607/115, 116, 136

(56) References Cited

U.S. PATENT DOCUMENTS

| | | |
|---|---|---|
| 4,261,372 | 4/1981 | Iiansen . |
| 4,284,085 | 8/1981 | Hansen et al. . |
| 4,686,765 | 8/1987 | Byers et al. . |
| 4,762,135 | 8/1988 | Van Der Puije et al. . |
| 4,795,458 * | 1/1989 | Regan ........................................ 623/1 |
| 4,832,051 | 5/1989 | Jarvik et al. . |
| 5,123,422 | 6/1992 | Charvin . |
| 5,545,219 | 8/1996 | Kuzma . |
| 5,578,084 | 11/1996 | Kuzma et al. . |
| 5,645,585 | 7/1997 | Kuzma . |
| 5,653,742 | 8/1997 | Parker et al. . |
| 6,074,422 | 6/2000 | Berrang et al. . |

OTHER PUBLICATIONS

"The Scala Vestibuli for Cochlear Implantation—Anatomic Study", A.J.Gulya et al., Arch. Otolaryngol. Head Neck Surg vol. 122, Feb. 1966, pp. 130–132.

"Dimensions of the Scala Timpani in the Human and Cat with Reference to Cochear Implants", S. Hatsushika. The Annals of Otology, Rhinology, and Laryngology, 99:1990, pp. 871–876.

(List continued on next page.)

*Primary Examiner*—David J. Isabella
(74) *Attorney, Agent, or Firm*—Paul Smith Intellectual Property Law

(57) ABSTRACT

A new surgical method and tools are described for the implantation of electrode arrays into the canalis cochlearis of profoundly deaf persons. Access to the canalis cochlearis is via the bony exterior ear canal and the middle ear, rather than the conventional route of drilling a cleft through the mastoid region posterior to the ear. Preferably entry to the canalis cochlearis is at a tangential angle to the curve of the basal turn.

A template is described for landmarking the site for tangentially drilling into the canalis cochlearis comprising a plate shaped to be positioned by reference to the round window of the middle ear and the oval window. A device for holding open the field of view for the surgeon during implantation comprises elongated funnels.

10 Claims, 16 Drawing Sheets

OTHER PUBLICATIONS

"A Tantalum–on–Sapphire Microelectrode Array", G.A.May et al. IEEE Transactions on Electron Devices, vol. ED–26, No. 12, Dec. 1979, pp. 1932–1939.

"A prototype flexible microelectrode array for implant–prothesis applications", M. Sonn et al. Medical and Biological Engineering, Nov. 1974, pp. 778–790.

"Cochlear Pathology n Prebycusis", H. F. Schuknecht and M. R. Gacek. The Annals of Otology, Rhinology, and Laryngology 102:1993.pp 1–15.

"Cochlear Implants", W.F.House. The Annals of Otology, Rhinology, and Laryngology, 85:1976, pp. 3–6.

"Four Years of Experience with Cochlear Prosthesis", I.J. Hochmair–Desoyer et al. Medical Progress through Technology, 8, 107–119 (1981).

"Computer–Aided Three–Dimensinal Reconstruction: A Method of Measuring Temporal Bone Structures Including the Length of the Cochlea", A.Takagi and I.Sando. The Annals of Otology, Rhinology, and Laryngology, 98:1989, pp. 515–522.

Prothèse Auditive par Excitation Electrique `` Distance du Nerf Sensoriel ``l'Aide d"un Bobinage Inclus `` Demeure A.Djuorno and C. Eyries. La Presse Médicale, 1957, 65,No. 63.

"Implantation of Multiple Intracochlear Electrodes for Rehabilitation of Tota Deafness: Preliminary Report", C.H.Chouard and P.Macleod.

"Cochlear Prostheses", G.M.Clark et al. Churchhill Livingstone, New York, 1990, Ch. 1, pp. 1–14.

* cited by examiner

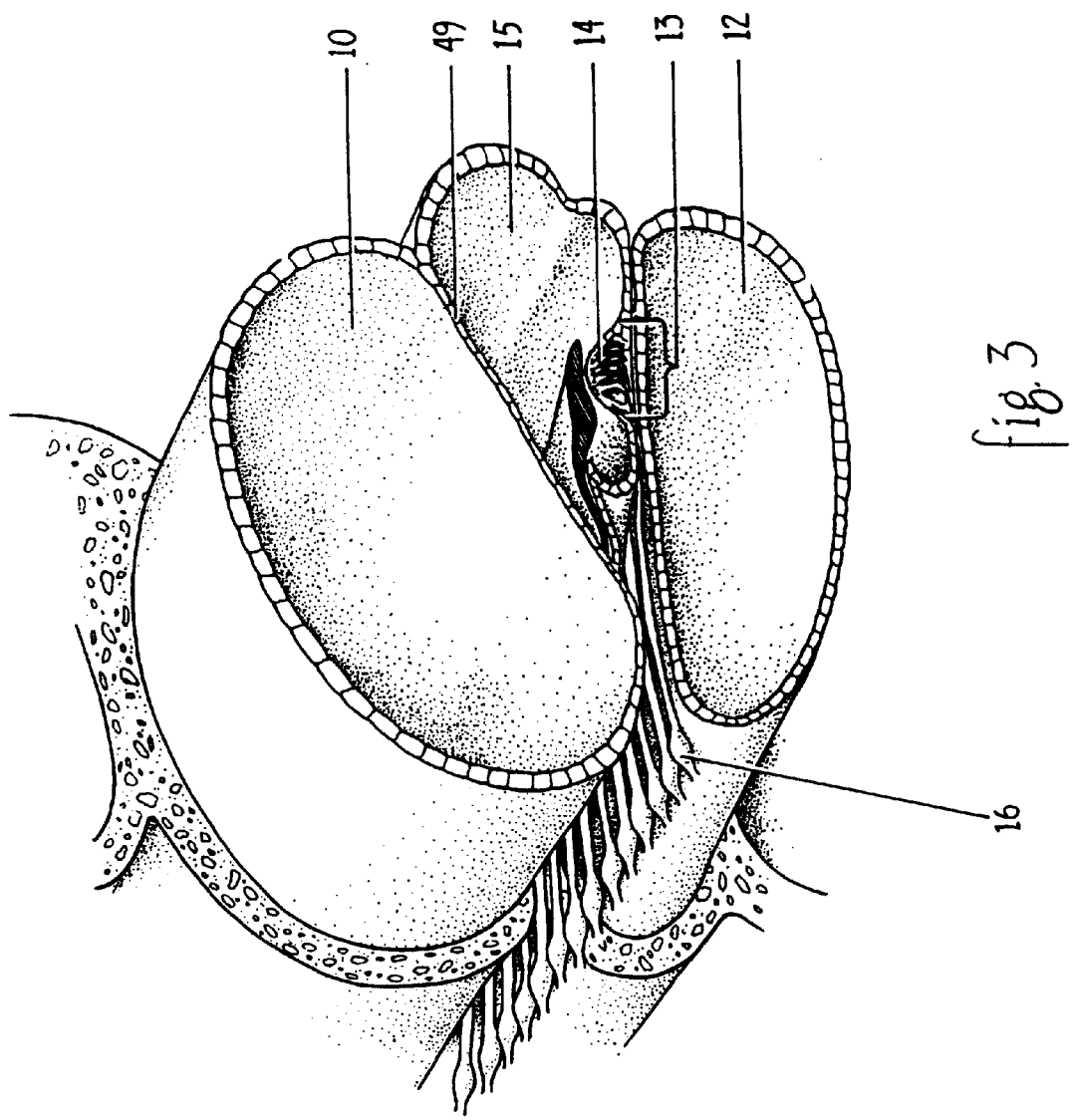

MEANS FOR IMPLANTING A DEVICE IN THE CANALIS COCHLEARIS

FIELD OF THE INVENTION

The invention relates generally to human hearing and more specifically to methods and tools for implanting a device in the canalis cochlearis (or cochlea) to generate auditory percepts in profoundly deaf persons.

BACKGROUND OF THE INVENTION

FIG. 1 illustrates how sound waves are collected by the outer ear 1 in humans to create hearing. Acoustic waves travel down the ear canal 2, wherein frequencies are enhanced in the 4,000 cycles/second range, and then impinge on the ear drum 3 causing it to vibrate in a complex manner. The ear drum transmits this vibrational energy to the three small bones, the malleus 4, the incus 5 and the stapes 6, which transmit and amplify the sound. These are located in the air space behind the ear drum, known as the middle ear 7. The acoustic energy is further transmitted by the innermost bone, the stapes, which fits like a plunger into a window in the cochlea known as the oval window 8, which is connected to the inner ear, or cochlea 52. The vibrational energy from the stapes is thereby converted to pressure waves within the cochlea, which contains two larger and one smaller channels which are arranged in a spiral fashion of approximately two and a quarter turns, as depicted in FIG. 2, which, for simplicity, is shown uncoiled.

The external sound is thus transmitted, firstly, into one channel of the cochlea 52, the scala vestibuli 10, where it travels to the apex of the channel. At the apex the pressure wave traverses an opening known as the helicotrema 11 into a second spiral channel, the scala tympani 12, continuing along this channel inside the spiral to the round window 9. This arrangement of two spiral channels, separated by a thin membrane, activates a sensitive mechanism known as the Organ of Corti 13 illustrated in FIG. 3. This contains approximately 15,000 hair cells 14 in each ear, in a central channel between the scala vestibuli 10 and the scala tympani 12, known as the cochlear duct 15. These are best illustrated in the sketch of the cross-section of the cochlear channels of FIG. 3. These hair cells respond to the sound originating from the ear canal and act essentially as bionic transducers that change acoustic energy into electrochemical neural responses. The latter are transmitted along the auditory nerve 16 to the brain, where the neural signals are processed in specialized areas of the brain by the auditory nuclei. These have far greater ability to develop in infants—a phenomenon known as brain plasticity. This is also the case in the learning of languages. It is therefore recognized that the ideal age for treatment of deafness is as early as possible, to take advantage of the brain's ability to adapt shortly after birth.

In many cases of deafness, the hair cells or the Organ of Corti are damaged, but the auditory nerves and their cell bodies are present in sufficient numbers to process speech if they are adequately electrically stimulated. This has been clearly described in numerous publications, including the seminal work by Harold F. Schuknecht, M.D, and Mark R. Gacek, M.D., Cochlear Pathology in Presbycusis, Annals of Otology, Rhinology, and Laryngology 1993;102:1–16 Supplement 158. This study suggested that hearing could be mediated electrically. Early attempts were made to stimulate the auditory nerve electrically during neurosurgical procedures or operations in which the auditory nerve was exposed, as in the case of Djoumo and Eyries (Prosthèse auditive par excitation électrique à distance du nerf sensoriel à làide d'un bobinage inclus à demeure, 1957, Presse Médicae35:14–17).

Modern developments to help the deaf include cochlear implant devices which pick up sound, process it, and deliver it in some way to the auditory nerve. Such developments have been well summarized by Clarke et al., *Cochlear Prostheses* edited by Graeme M. Clark; Yit. Tong & James F. Patrick, Churchill Livingstone, Edinburgh, London, Melbourne and New York, 1990. ISBN 0-443-03582-2.

Numerous inventions have been made regarding the implantation of electrodes to stimulate the auditory nerve. Chouard implanted multiple electrodes in the bony wall of the cochlea and later into the inner ear, as related in Chouard CH, McLeod P. 1976, Implantation of multiple intracochlear electrodes for rehabilitation of total deafness, Preliminary Report, Laryngoscope 86. 1743–1746. Similarly, Michelson and House experimented with intracochlear electrodes (William F. House, 1976. Cochlear Implants. Annals of Otology, Rhinology and Laryngology, Supplement 27, Vol. 85, May/June 1976, No. 3, Part 2), as did Hochmair-Desoyer IJ et al. (Four Years of Experience with Cochlear Prostheses, 1981, Medical Progress through Technology, Springer-Verlag, Vol. 8, pp. 107–119). More recent developments are summarized in the Proceedings of the European Symposium held in Hanover in June 1996 (American Journal of Otology, November 1997 Supplement. Lippincott-Raven).

Commercial cochlear implants currently available rely on surgery (see FIG. 4a) which places electronic parts 17 in the bone behind the ear known as the mastoid region 18 by drilling a small aperture 19 from the air cells in the mastoid region into the posterior part of the middle ear between the ear drum and the facial nerve 20. This nerve shown in cross-section in FIG. 4a, supplies the muscles of the face. Through this cleft electrodes are inserted either through or adjacent to the round window 21of the cochlea 52. Using this approach, access is obtained into the scala tympani.

The prior art approach described above is rather lengthy and has other significant limitations. The surgery is generally required to be done under general anesthetic, and the surgeon must navigate around several sharp bends which hinders full insertion of the electrode array into the scala tympani. Also, this approach requires significant drilling of the mastoid bone which creates a degree of bleeding from the bone vessels and marrow and provides a large raw bone surface area open to infection during surgery. Moreover, since the mastoid air cell system does not develop until approximately two years of age, this surgery is not possible for newborns. The bony dissection is extensive and there is a risk of damage to the facial nerve. The small access into the cochlea through the gap between the facial nerve and the tympanic membrane makes insertion of the flexible, delicate electrode array fully into the scala tympani very difficult and imposes a curvature in the line of insertion (see FIG. 4a). The present invention provides an improved method for surgically implanting a cochlear implant which overcomes these limitations of the prior art approach.

In our co-pending application entitled Inner Ear Implant Device filed contemporaneously with this one, the disclosure of which is incorporated herein by reference, a cochlear implant is described which comprises two elongated electrode-bearing prongs allowing insertion of one prong into the scala tympani and the other prong into the scala vestibuli for improved hearing percepts by the patient. It is an object of the present invention to provide a method for surgically implanting a cochlear implant as described in our co-pending application. It can also be adapted for use with conventional electrode arrays.

Surprisingly, the dimensions of the cochlea are remarkably constant from infancy to adulthood. Numerous anatomical studies of the scalae have been made, for example, see Takagi A, Sando I., Computer-aided Three-dimensional Reconstruction: A method of Measuring Temporal Bone Structures Including the Length of the Cochlea, Annals of Otology Rhinology and Laryngology, 1989, 98:515–522. These dimensions are critical in the design of any tools or methods to implant optimum performing stimulation devices into the cochlea of deaf persons. It is a further object of this invention to take advantage of the consistency in the dimensions of the cochlea by providing a template for use in assisting the surgeon in implanting a cochlear implant using the method of the invention.

It is yet a further object of the invention to provide a tool for keeping the surgeon's field of view unobstructed during surgery according to the method of the invention.

Current implant data suggest that proximity of electrodes located near the inner wall of the cochlea, where the nerves gather into the central "core" of the cochlea (modiolus), as well as the density of electrodes, have a positive effect on the performance of the implantee's speech percepts. Since present electrode arrays tend to position themselves naturally along the outside wall of the scala tympani during surgical implantation, it is difficult to stimulate discrete areas where nerve cells may still be functional. Thus, the consensus appears to be that it is better to position the electrodes as close as possible to the modiolus, as evidenced by the many designs that have attempted to orient the electrode array to get closer proximity to the modiolus. For example, Hansen et al. in U.S. Pat. No. 4,284,085 describes an implant design that uses "tabs" which contact the inner wall of the cochlea to enhance both the positioning and the proximity of the electrodes to the auditory nerves. Byers et al. in U.S. Pat. No. 4,686,765 details a method for manufacturing a preshaped electrode that preferentially curls to the inner wall of the cochlea. Kuzma further describes a method for altering the shape of an electrode in situ through the use of bio-absorbing materials to engage the inside turn of the cochlea in U.S. Pat. No. 5,578,084. Parker et al. details the use of bio-resorbable materials to allow an electrode to change shape after insertion in the cochlea in U.S. Pat. No. 5,653, 742. In U. S. Pat. No. 4,261,372 Hansen teaches a multiple prong electrode design for addressing different turns within the same scala of the cochlea to achieve maximum insertion distance. It is therefore a further object of the invention to provide a means for ensuring that the electrodes of a cochlear implant are positioned as close as possible to the walls of the scalae.

The foregoing and other objects of the invention will be discerned from the summary of the invention and the detailed description of the preferred and alternative embodiments which follow.

SUMMARY OF THE INVENTION

This invention provides an improved surgical technique for implanting a cochlear prosthesis for the profoundly deaf, and associated tools for use in such surgery. Such improved means will be more effective in allowing the implantee to hear and understand normal speech, and appreciate at least some element of music.

According to one of its aspects the invention is a method of implanting a prosthesis in the cochlea wherein access to the cochlea is via the bony external ear canal and the middle ear. A postauricular incision is made and the middle ear is approached under the skin of the bony external ear canal such approach including displacing the annulus. A hole in the cochlea is drilled in the basal turn of the cochlea at an angle of substantially 15 to 20 degrees in relation to the normal to the basal turn of the cochlea, in the direction of the hypotympanum.

In another of its aspects, the invention comprises a template for landmarking an optimum drill site in the inner ear for gaining access into the scalae as part of a cochlear prosthesis implant operation comprising a thin flat plate adapted to fit against the promontory of the cochlea and comprising features indicative of the relative position of said drill site in relation to the centre of the round window, and to the centre of the round window membrane.

In another aspect the invention is a method of implanting a prosthesis into at least one scala of the cochlea wherein access to the cochlea is via the external ear canal, an opening is made in the first turn of the cochlea using a substantially tangential approach to the basal turn of the cochlea and an elongated speculum is inserted either through the external ear canal or into a post auricular incision to maintain a clear field of view for the surgeon.

In yet another aspect, the invention is a method of implanting an electrode array into at least one scala of the cochlea comprising the steps of implanting said array while said array is rolled or coiled around a catheter-like tube, and of inflating said tube after implantation so as to partly unroll or uncoil said array to position the electrodes in close proximity to the scala walls. In a more particular aspect, the electrode array has two prongs, each of said prongs is rolled or coiled around a catheter-like tube, each of said prongs is inserted into a different scala and each of said catheter-like tubes is inflated after implantation.

In another aspect, the invention is a speculum for use in inner ear surgery comprising a generally funnel-like shape, a larger end having a diameter of approximately 35 mm and a milled periphery providing a grippable surface, and an overall length of greater than 40 mm. The speculum may or may not have a slot running the length of the speculum, to allow the electrode array to be slid through the slot after implantation in the cochlea.

The invention provides for a much shorter surgical time. Surgery for existing implants generally requires 3–4 hours, during which time the patient is under total anesthesia. The invention detailed herein allows for surgical time to be approximately one hour or less, with some patients needing only a local anesthetic. This aspect is critical for infants and the elderly who have poor ability to withstand long anesthetics.

This novel surgical method greatly simplifies implant surgery and reduces the risk of damaging delicate intracochlear structures. Such method also allows the surgeon to use only local anesthetic for some patients, whereas conventional surgery requires total anesthesia. The use of only a local anesthetic, in addition to accessing the cochlea via the ear canal allows for implantation into newborns, heretofore not possible.

Additionally, the invention describes a surgical route that does not risk damaging surrounding structures such as the facial nerve, which is a critical issue with the current art. The surgery described herein provides for far less bleeding, and therefore less collection of free blood to develop infection. Finally, since the preferred embodiment of the surgery does not necessarily involve drilling a relatively large hole in the mastoid bone, the inventive surgical procedure is amenable for newborns, a group that could heretofore not be accommodated using the current art.

The inventive procedure to expand a coiled electrode array during surgery enables the electrodes to be positioned more optimally, that is, closer to the walls of the cochlea, especially nearer to the modiolus, and nearer any remaining residual processes in the basilar membrane.

Other features of the invention, including more specific ones, are defined by the claims and will become apparent from the following detailed description of the preferred and alternative embodiments.

BRIEF DESCRIPTION OF DRAWINGS

The preferred and alternative embodiments of the invention will be described by reference to the accompanying drawings, in which:

FIG. 3 is a perspective cross sectional view of the canals of the cochlea.

DESCRIPTION OF THE PREFERRED AND ALTERNATIVE EMBODIMENTS

In this description, anterior is towards the front, posterior is towards the rear, superior is up, and inferior is downwards. Clockwise etc. refers to the most superior or upwards area of the eardrum (tympanic membrane) as 12:00 o'clock. The implant can be inserted by any approach which gives access to the basal turn of the cochlea, however the procedure is carried out by a transcanal approach along the edge of the back of the bony ear canal either through an endaural or postauicular tympanotomy incision, rather than through the mastoid bone.

Figure 5:
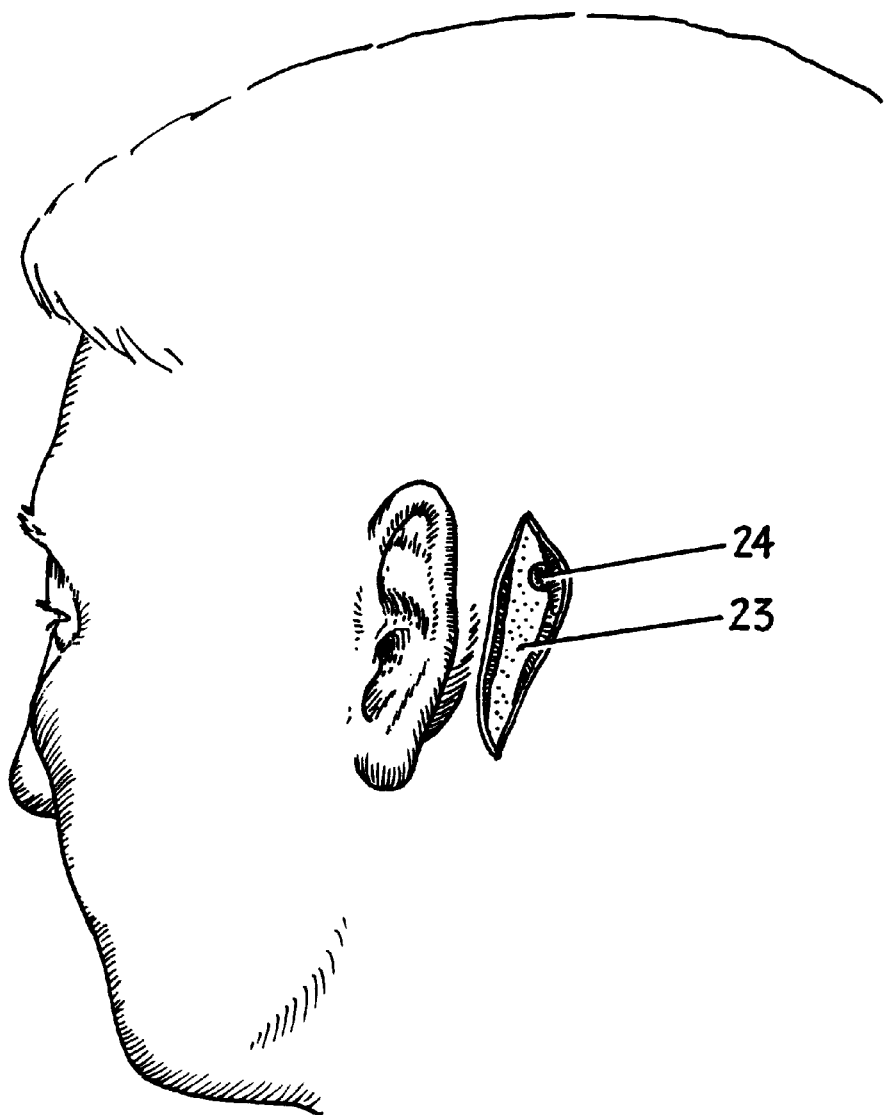
FIG. 5 is a view of the patient's head from an oblique posterior viewpoint showing the site of the initial skin incision behind the ear according to the inventive method.

Surgery for insertion of the implant according to the invention can be performed under local or general anesthesia, with or without sedation. FIG. 5 shows where an initial skin incision 23 behind the ear is made. An opening 24 in the skin for a transcutaneous pedestal is also made.

Figure 6:
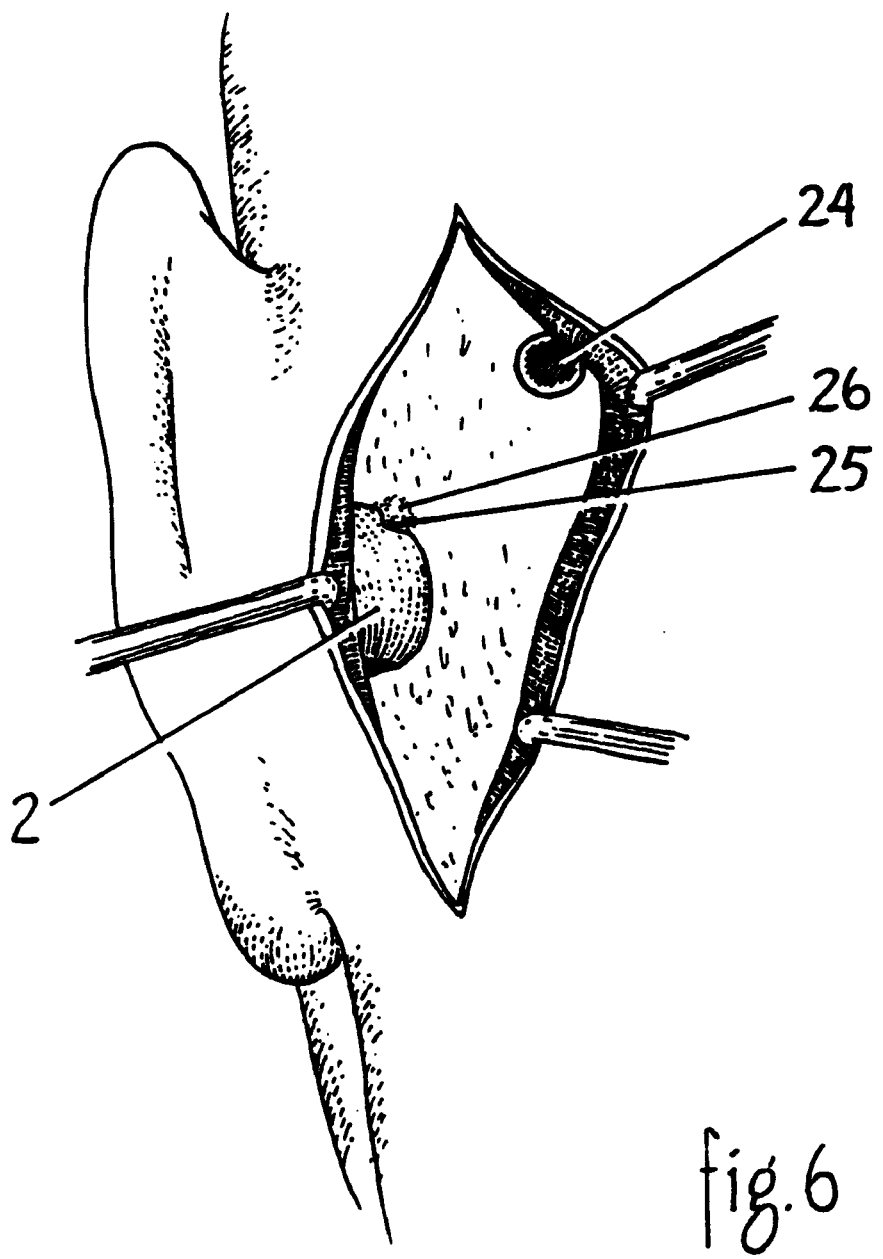
FIG. 6 is a close up view of the same patient as in FIG. 5 showing the development of the surgery through the post-auricular skin incision to expose the bone of the external auditory canal.

Further dissection is performed to expose the bone of the external ear canal. FIG. 6 shows the surgical exposure through the post-auricular incision down to the bone of the external ear canal. The ear canal 2 may be narrowed at the bony meatus where a small spine (the spine of Henle 25) and a triangle of bone (McEwens triangle 26) may be seen. Some bone may be removed here to enlarge the bony meatus into the bony external ear canal. Dissection down the posterior and inferior part of the bony external canal, under the skin of the canal is made to join up with the internal incisions described below. Possible locations for the transcutaneous pedestal are indicated by the numeral 24.

Figure 7:
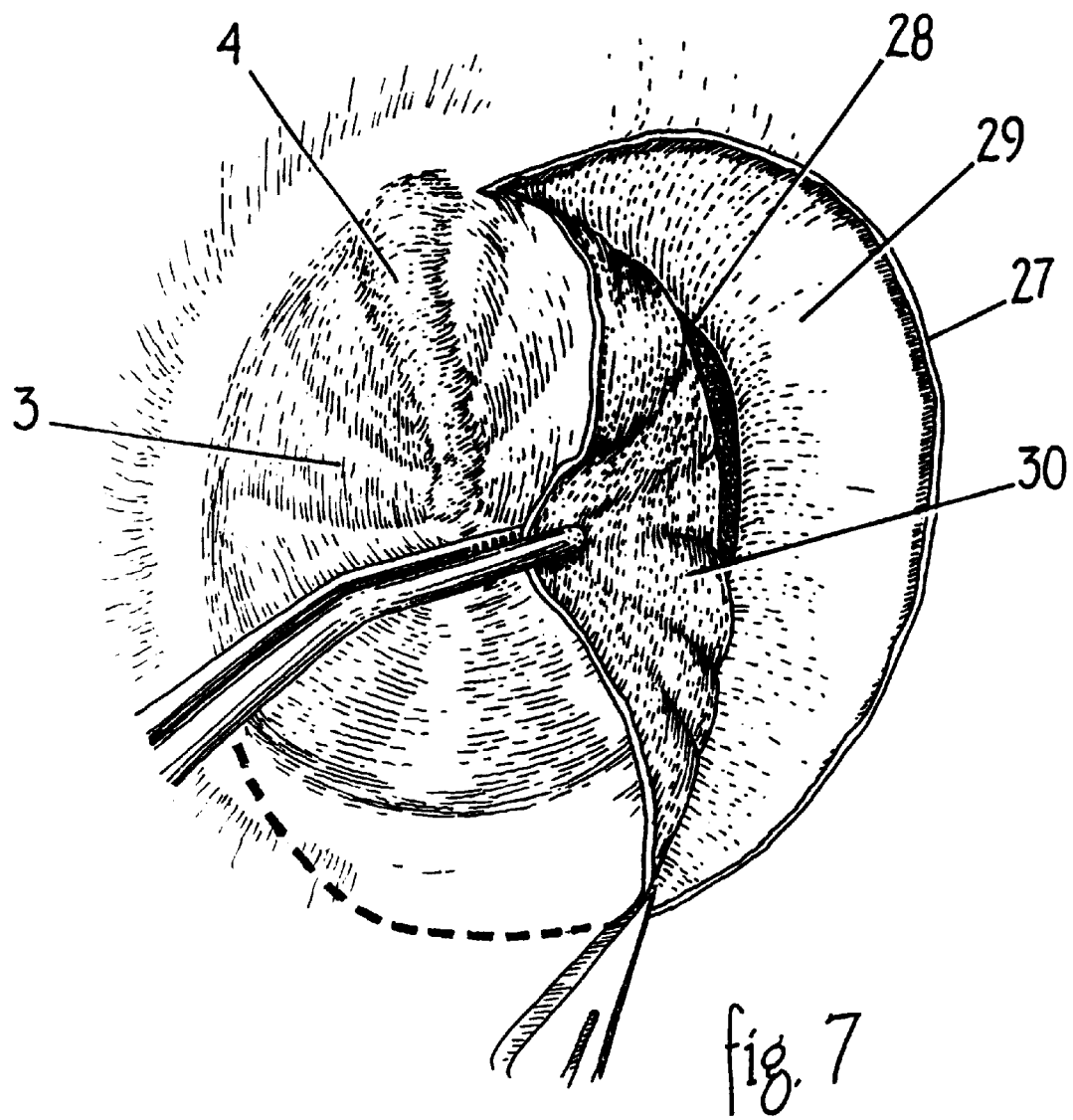
FIG. 7 is a surgeon's view of the dissection showing the incision of the skin within the external auditory canal exposing the bone of the external auditory canal.
Figure 8:
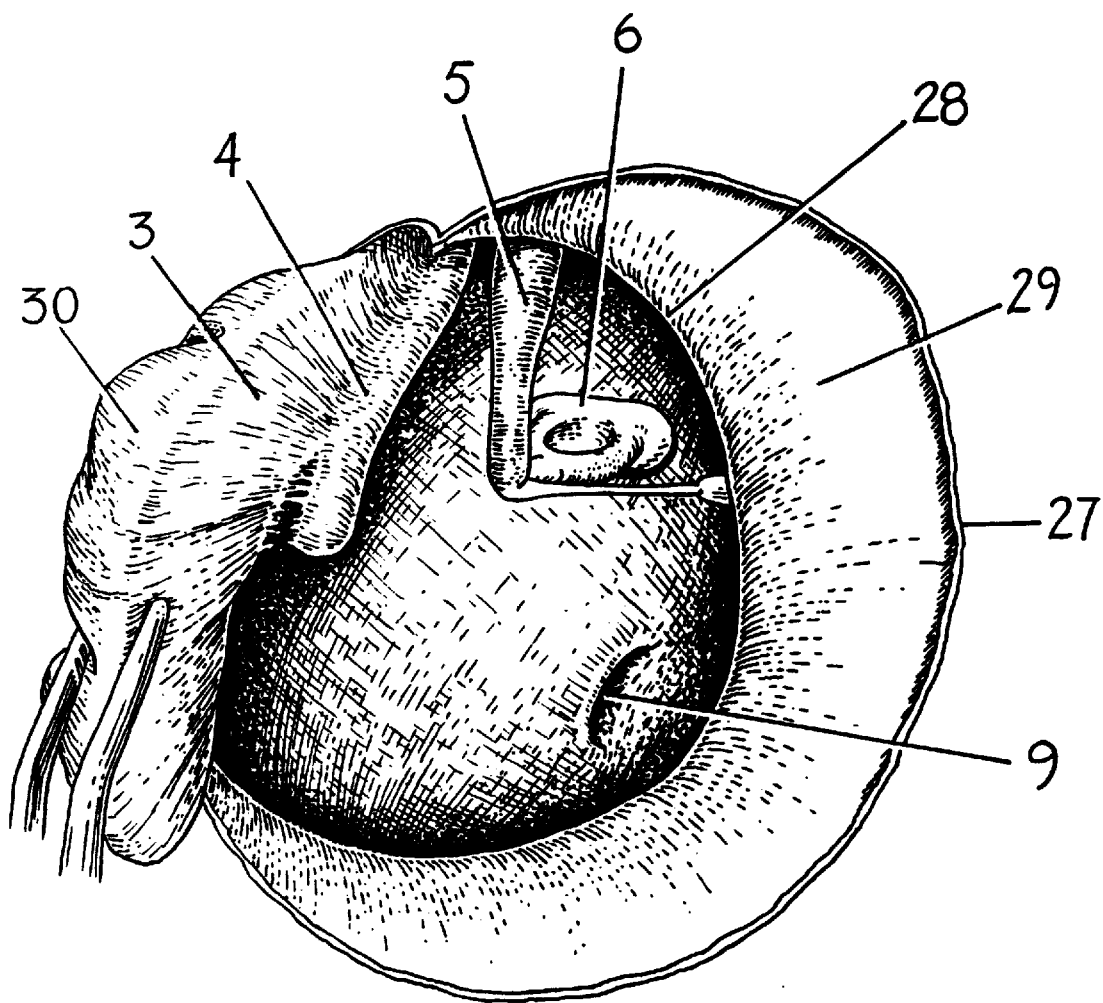
FIG. 8 is a surgeon's view of the dissection showing the view of the middle ear and its landmarks as seen through the external auditory canal.

FIG. 7 shows the tympanic membrane 3 and adjacent bony ear canal 29. A small amount of adrenaline or similar vasoconstrictor with local anesthetic is injected into the external canal in an amount sufficient to raise "blebs". A transcanal tympanotomy incision is made in the bony canal 27 approximately 4 mm posterior to the annulus of the tympanic membrane 28 and from approximately superiorly to directly anteriorly swinging through a posterior curve. In the case of the right ear, this is from approximately 11:00 o'clock to 3:00 o'clock passing anti-clockwise. In the case of the left ear, this is from approximately 1:00 o'clock to 9:00 o'clock passing clockwise. This incision is continued separating the skin of the bony external auditory canal 3 from the bone of the external ear canal 29. A posterior tympanotomy flap 30 is raised (FIG. 8) and extended under the annulus 28, exposing the posterior and inferior part of the middle ear. In doing so, the annulus or thickened edge of the ear drum is dislocated forward from the bony annulus of the ear canal 28.

Figure 9A:
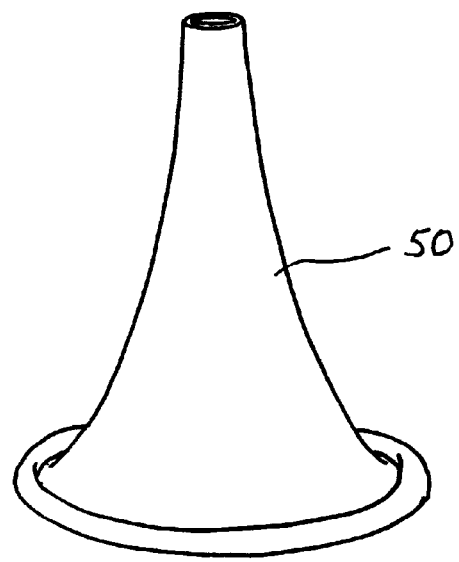
FIG. 9a is a perspective view of a speculum according to the invention.
Figure 9B:
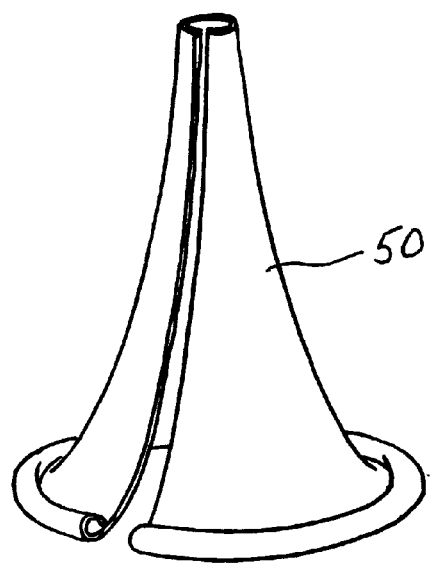
FIG. 9b is a perspective view of a speculum according to the invention with a slot along its length.

A special speculum has been designed for use in this procedure. The speculum acts to hold the soft tissues out of the line of the surgeon's view while still allowing the surgeon to view the inner ear. Prior art speculae used for inner ear surgery are limited to 40 mm in length. In the case of the present invention, which uses a surgical route not previously used, a longer speculum is necessary. Accordingly, a speculum 50 as illustrated in FIG. 9a or 9b is used. Speculum 50 comprises a funnel-like shape wherein the large end has a diameter of approximately 35 mm and the periphery of the large end is milled to provide a surface for gripping by the surgeon. Preferably such milling produces a series of closely spaced ridges. Speculum 50 is more than 40 mm in length, and is preferably available in lengths of 42, 44, 46, 48, 50 and 52 mm. The diameter and shape of the small end of the speculum should be those dimensions and shapes available in prior art speculae. The speculum can also be slotted for access of instruments and devices used in the surgery as illustrated in FIG. 9*b*.

Figure 10:
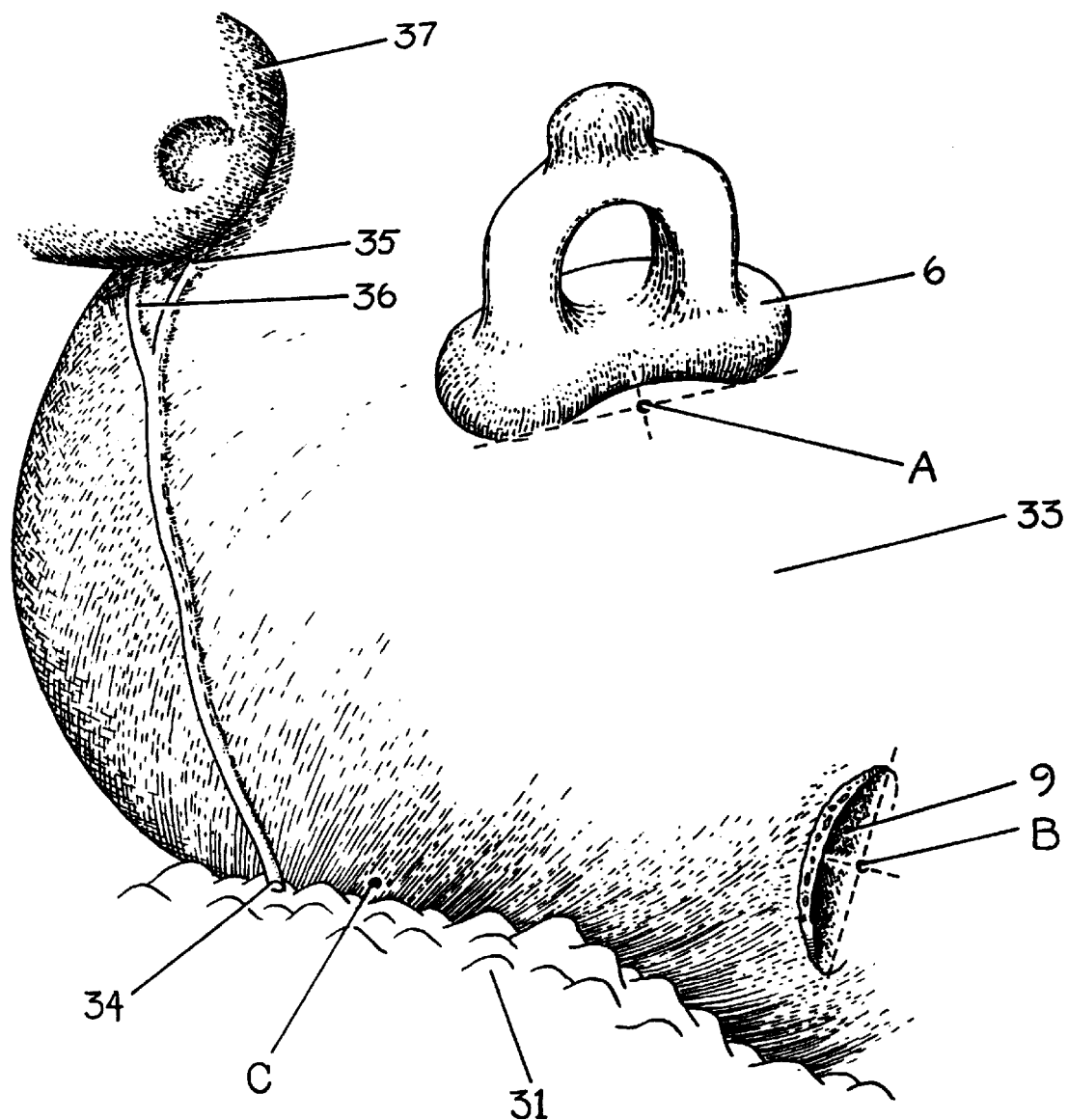
FIG. 10 is a surgeon's view of the dissection showing the medial wall of the middle ear and the landmarks and points "A", "B", and "C"

The middle ear is entered and the main landmarks are identified, as best appreciated by reference in FIG. 10. These are the stirrup (stapes) 6, the round window 9, the hypotympanum 31 (the irregular bony lower part of the middle ear), and the tympanic nerve 32, a nerve on the surface of the medial or inwards surface of the middle ear on a protuberant area called the promontory 33. Here the tympanic nerve lies in a groove or canal over the promontory. It appears in the middle ear from its canal 34 in the hypotympanum 31 and usually disappears through one or more canals (35, 36) superiorly just below the process us cochleariformis 37.

Figure 11:
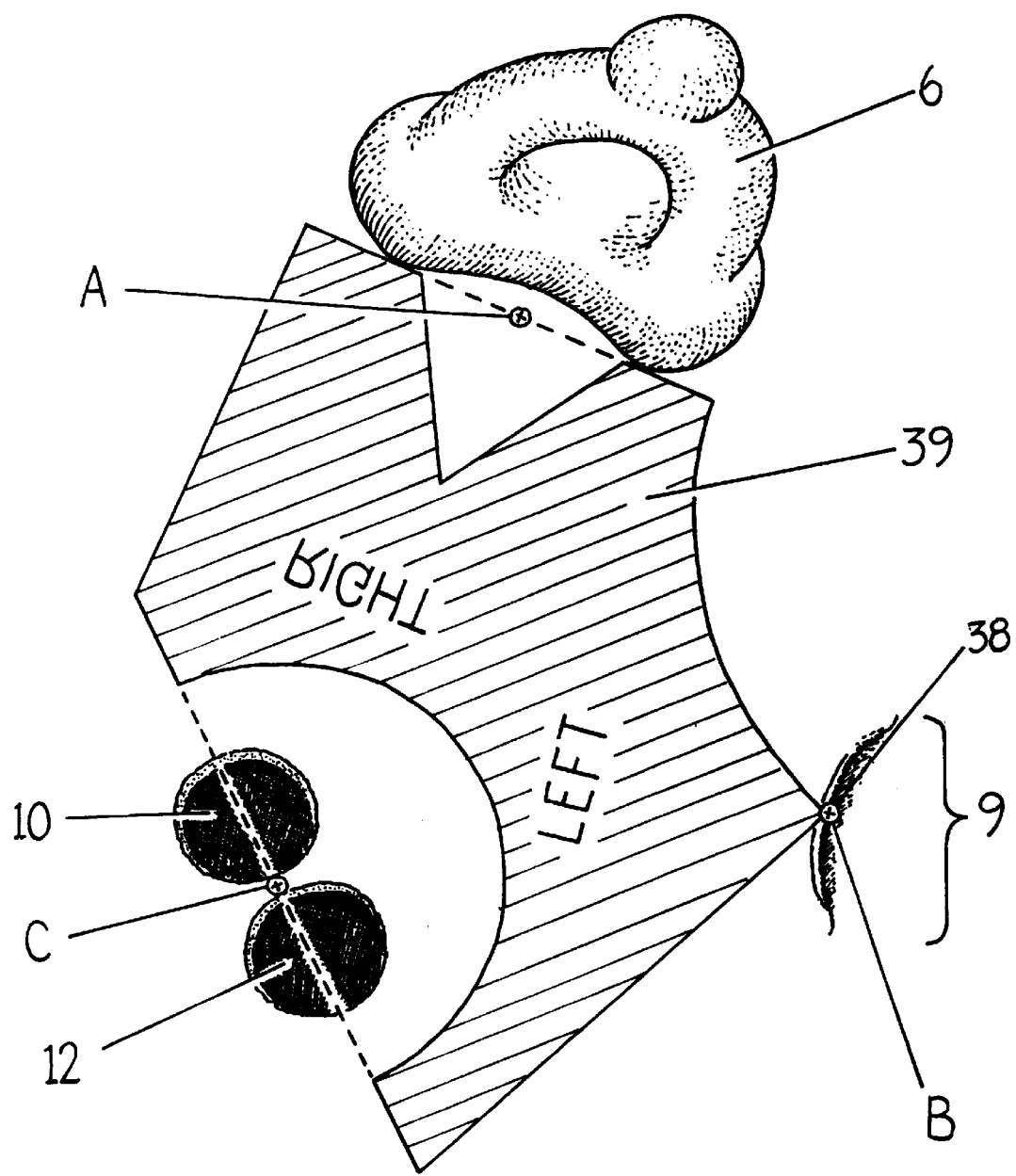
FIG. 11 is a surgeon's view of the dissection showing the template in place on the medial wall of the left middle ear, lying on the wall of the cochlea.

Once the landmarks of the middle ear are identified, parts of the malleus, incus, or stapes can be partially removed if necessary to gain access to the promontory. In front of the round window, a crescent of bone (the crista semilunaris) is removed, to allow vision of the round window membrane 38. The tympanic nerve is cauterized at the point at which it leaves canal 34 in the hypotympanum 31 and at the upper extent of its branch or branches, where it starts to leave the superior part of the promontory (35,36) and run under the processus cochleariformis 37. FIG. 11 also shows where a point is located at the centre of a line connecting the inferior extents of the kidney shaped margin of the oval window, that is the foot-plate of the stapes. This is designated point A. The second point is located at the centre of the round window membrane and this is designated point B. A further point is located where the bulge of the promontory, which overlies the first turn of the cochlea, meets the hypotympanum. This new point is designated point C.

Figure 12:
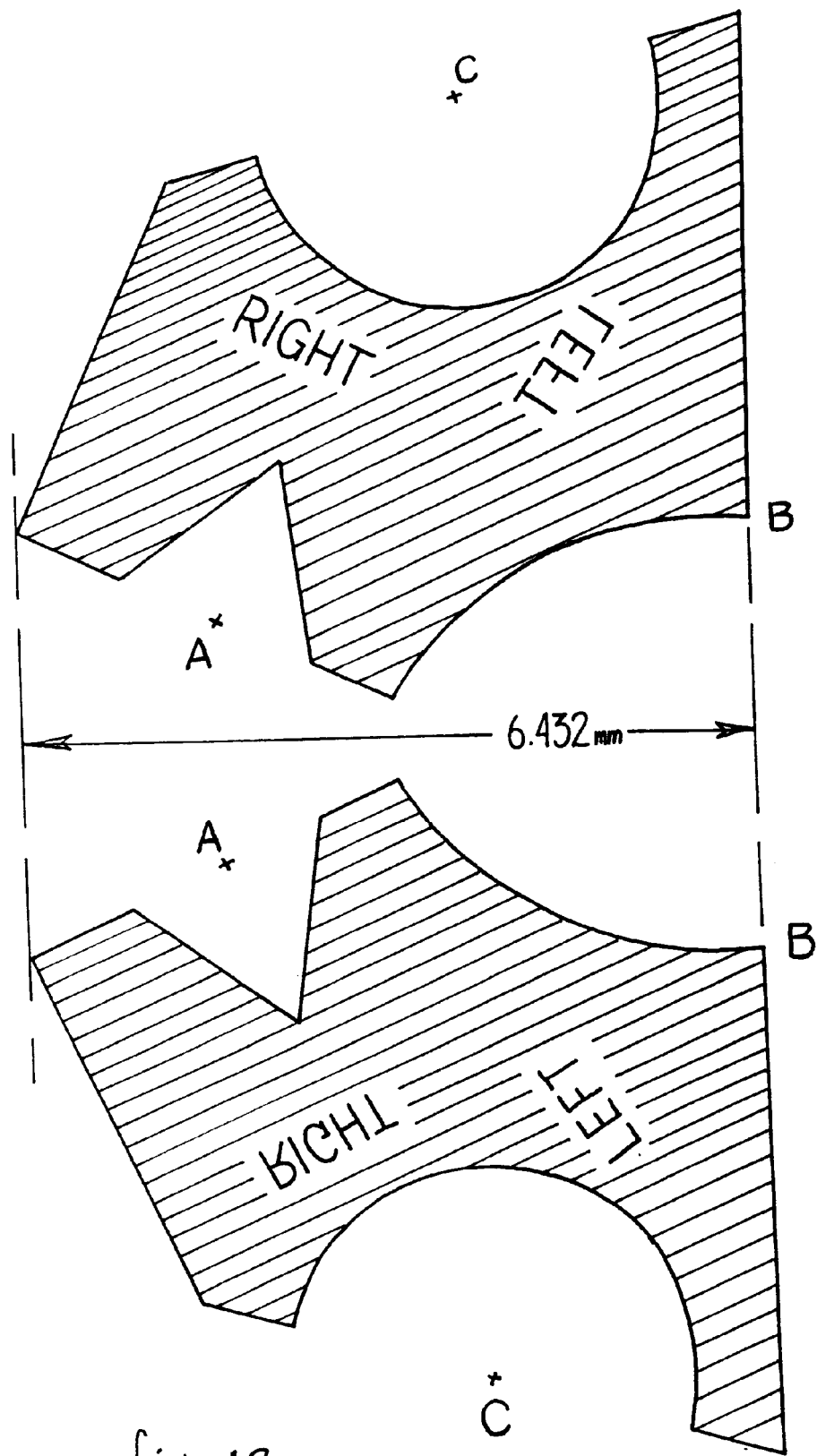
FIG. 12 is a plan view of two sides of the template according to the invention.

There is a variation in different ears, but in order to approximate the most common anatomical locations of these landmarks, a template 39 has been developed. The template's general shape is illustrated in FIGS. 11 and 12. It is composed of a thin flat sheet of material which is sufficiently flexible to be passed through a narrow speculum of the type described below. The template is cut into a shape such that if the point "A" is placed in the middle ear, over the centre of the inferior margin of the oval window and point "B" is placed over the centre of the round window membrane, then point "C" indicates the centre in which the surgeon may drill in order to expose the scala vestibuli and scala tympani at a tangential point in the basal turn of the cochlea. This template 39 is placed over the promontory on the medial wall of the middle ear, lying on the wall of the cochlea 52 in the appropriate alignment with points A and B as noted above. Point C is the centre of the area to be drilled out for access to the scala tympani and the scala vestibuli. It is marked and the template is removed either with a handle or a string to ensure its retrieval.

Figure 1:
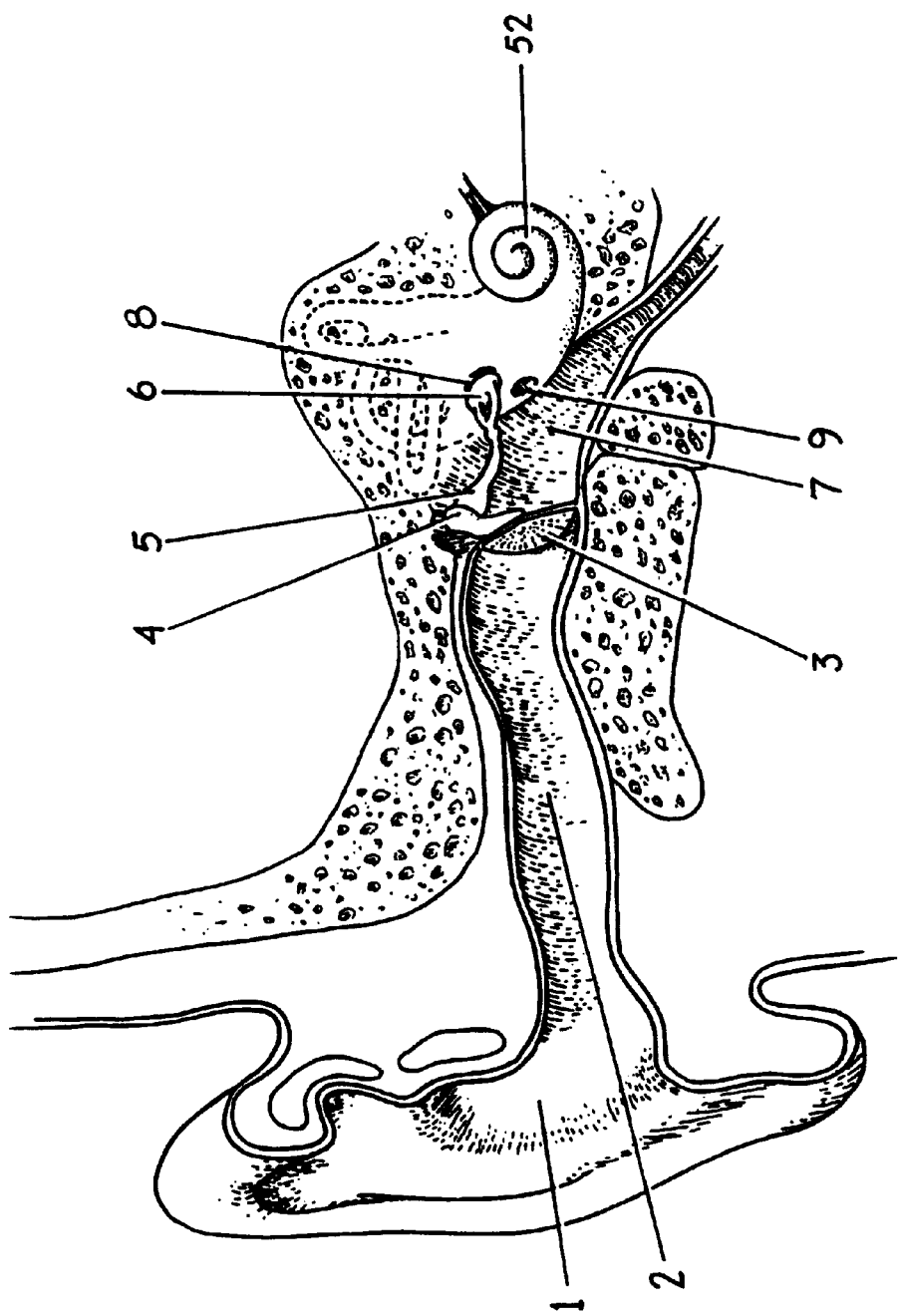
FIG. 1 is a coronal section view of the general anatomical features of the human ear.
Figure 2:
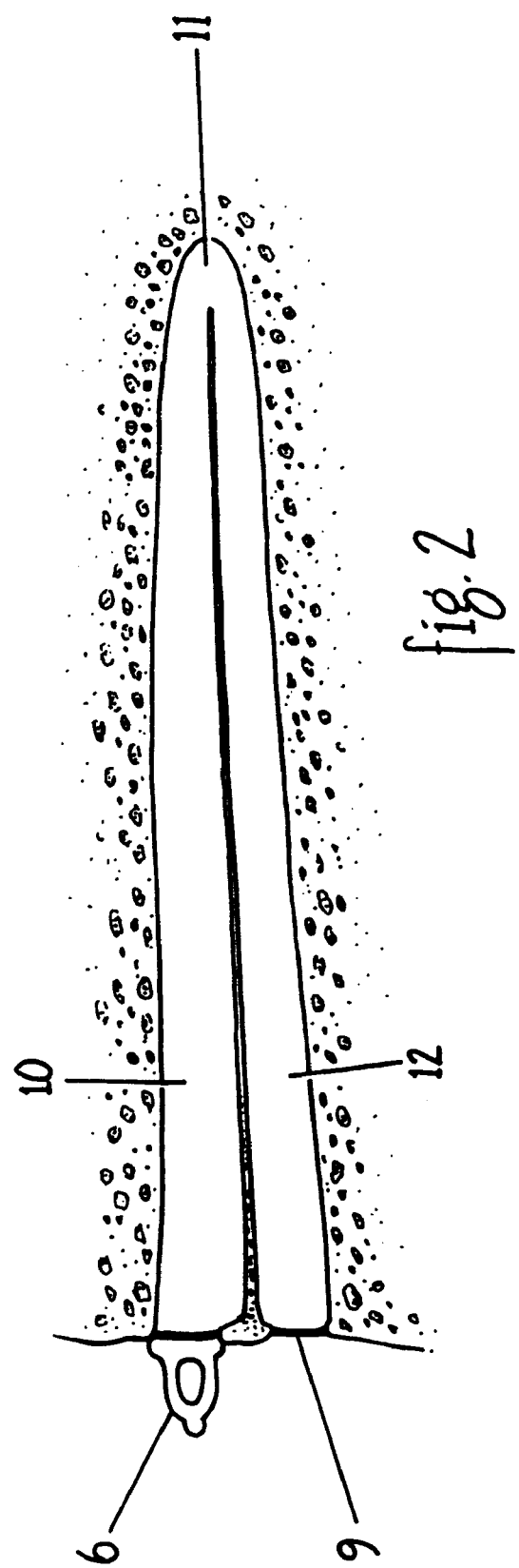
FIG. 2 is a longitudinal cross section view of the cochlea, showing the cochlea as it would appear if it were uncoiled.
Figure 4A:
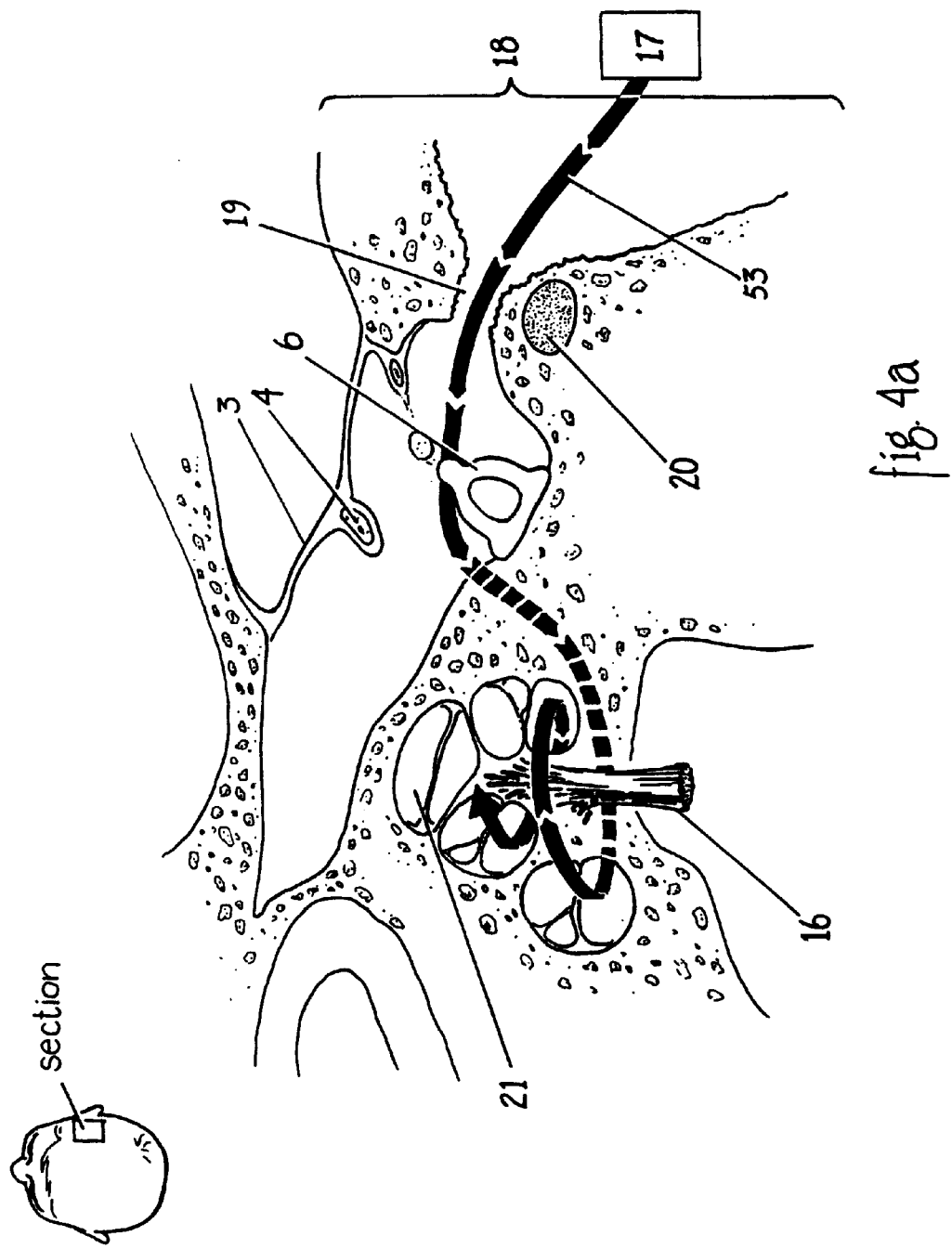
FIG. 4a is a superior plan sectional view of an actual human ear illustrating the route of implantation of cochlear implants according to the prior art.
Figure 4B:
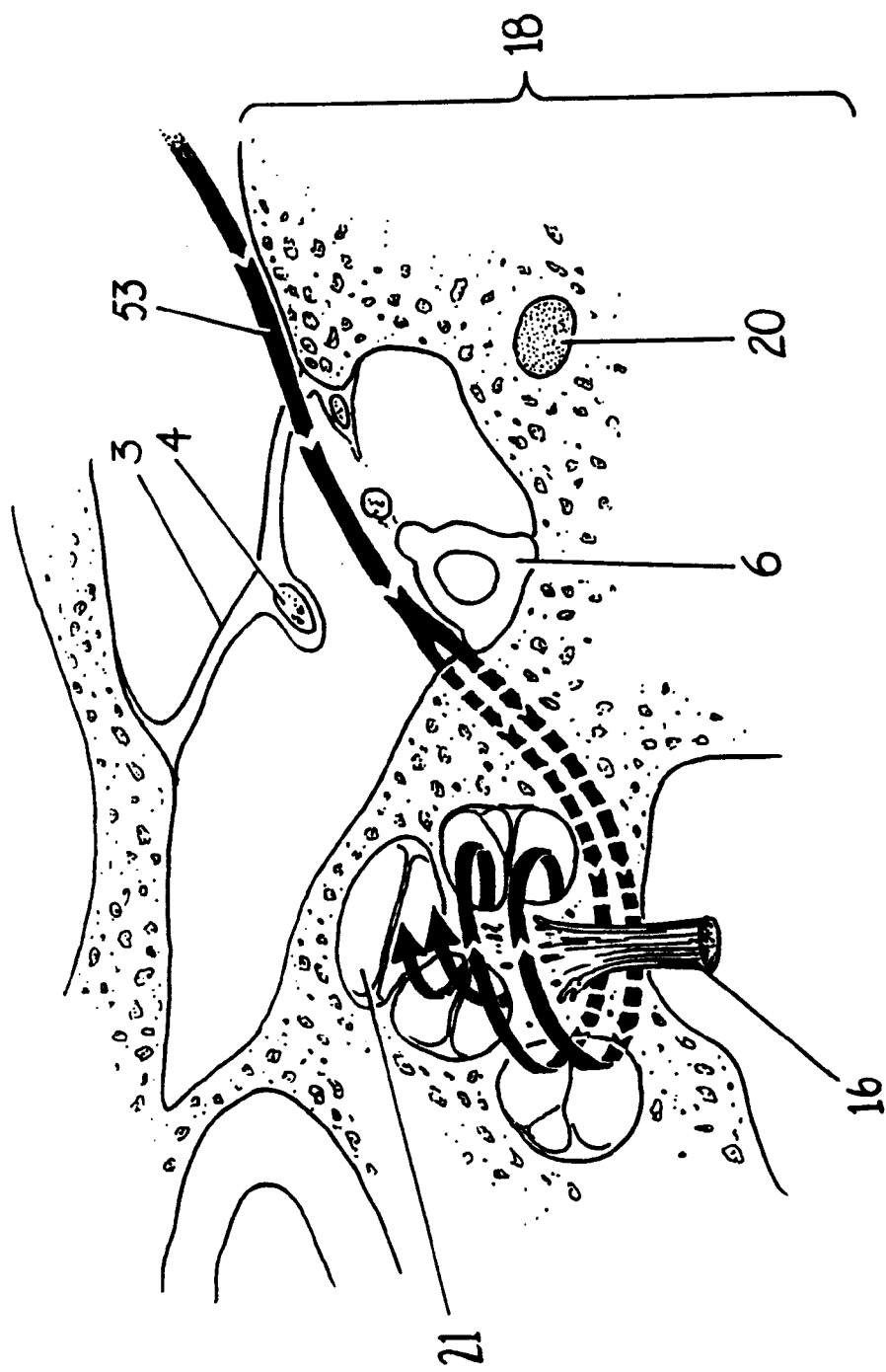
FIG. 4b is a superior plan sectional view of an actual human ear illustrating the route of implantation of cochlear implants according to the invention.

It should be noted that this method gives access to one or both of the scalae, approximately at a tangential point in the basal or first turn of the cochlea close to the hypotympanum. At this point, the scalae are pointing the most directly away from the surgeon in the case of surgery through the ear canal (see the horizontal section through the ear region in FIG. 4*b*).

Access to the scalae through the basal turn provides a significantly simpler approach 53 than the prior art in that fewer sharp turns need to be navigated to achieve good insertion depth of the electrodes. In order to access the scalae from the basal turn, the hole to be drilled should not be directly normal to the apex of the basal turn, but rather should be at an angle of about 15 to 20 degrees from the normal towards the hypotympanum.

The surgical procedure described herein allows for insertion (FIG. 13) of various types of electrodes arrays into either the scala tympani or scala vestibuli, or both. The following discussion contemplates the implantation of an electrode array disposed on an implant comprising two prongs attached to a common base, wherein one prong is implanted into each of the scala tympani and the scala vestibuli. Such an implant is described in our co-pending application entitled Inner Ear Implant Device filed contemporaneously herewith. The implant in question is a flexible, planar electrode device 40, fabricated from a biocompatible metal, supported by an inert, non-conductive carrier, with preferably two electrode prongs where said prongs 41, 42 can be inserted one in each scala.

Two cylindrical openings into respectively the scala vestibuli and the scala tympani (10,12) each approximately 1 mm in diameter (or a conjoined cavity including both) are drilled through the bone of the promontory, centred at point C as described above. It is very important at this stage to keep the field clean and cool for example by the use of irrigation and suction. By this means access is gained to the inferior extent of the first turn of the cochlea as it meets the bone of the hypotympanum and starts to wind anteriorly and medially away from the surgeon. Openings are made into either the scala tympani or the scala vestibuli or both using either a drill with suction irrigation with a substance such as normal saline, or with a laser. A lubricant such as hyaluronidase may be injected into the scalae, and antibiotics may be injected into the scalae.

Figure 13:
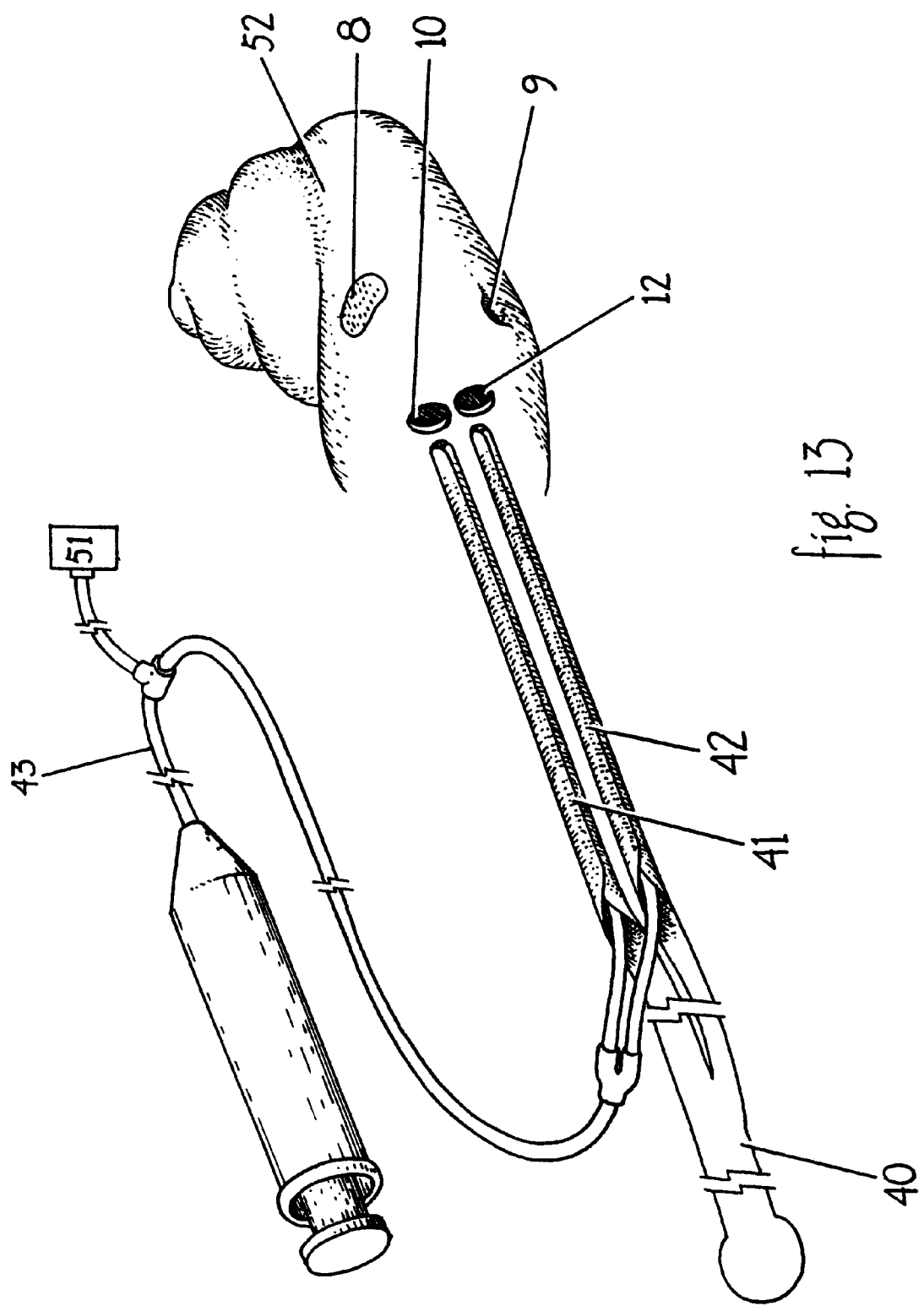
FIG. 13 is a diagram of the surgeon's view of the dissection showing the openings made into the scala(e) and the electrode implant and expanding means ready for insertion.

The two openings are spaced from one another but the directions of drilling will be parallel. Once the openings in the scalae are made, the prongs of the implant may be inserted in their respective scalae. Prior to insertion of the electrode device 40, its prongs are coiled or rolled up about their longitudinal extent around an expandable catheter-like tube 43, as shown in FIG. 13. The outside diameter of the coiled-up electrode array must be smaller than the diameter of the scala to allow the electrode array to be inserted into one, or both, scalae.

After insertion of the electrode array, the coil of the array is expanded such that the array uncoils, insofar as is possible within the confines of the scala, to thereby be seated in closer proximity to the walls of the cochlea in each scala. The effect of the electrode arrays' being closer to the basilar membrane and modiolus is a great advantage in that such positioning allows for a narrowly focused current density needed to stimulate the nervous mechanisms and more electrodes can be used with minimal cross-talk effects. As a result the patient can acquire improved hearing percepts.

Figure 14:
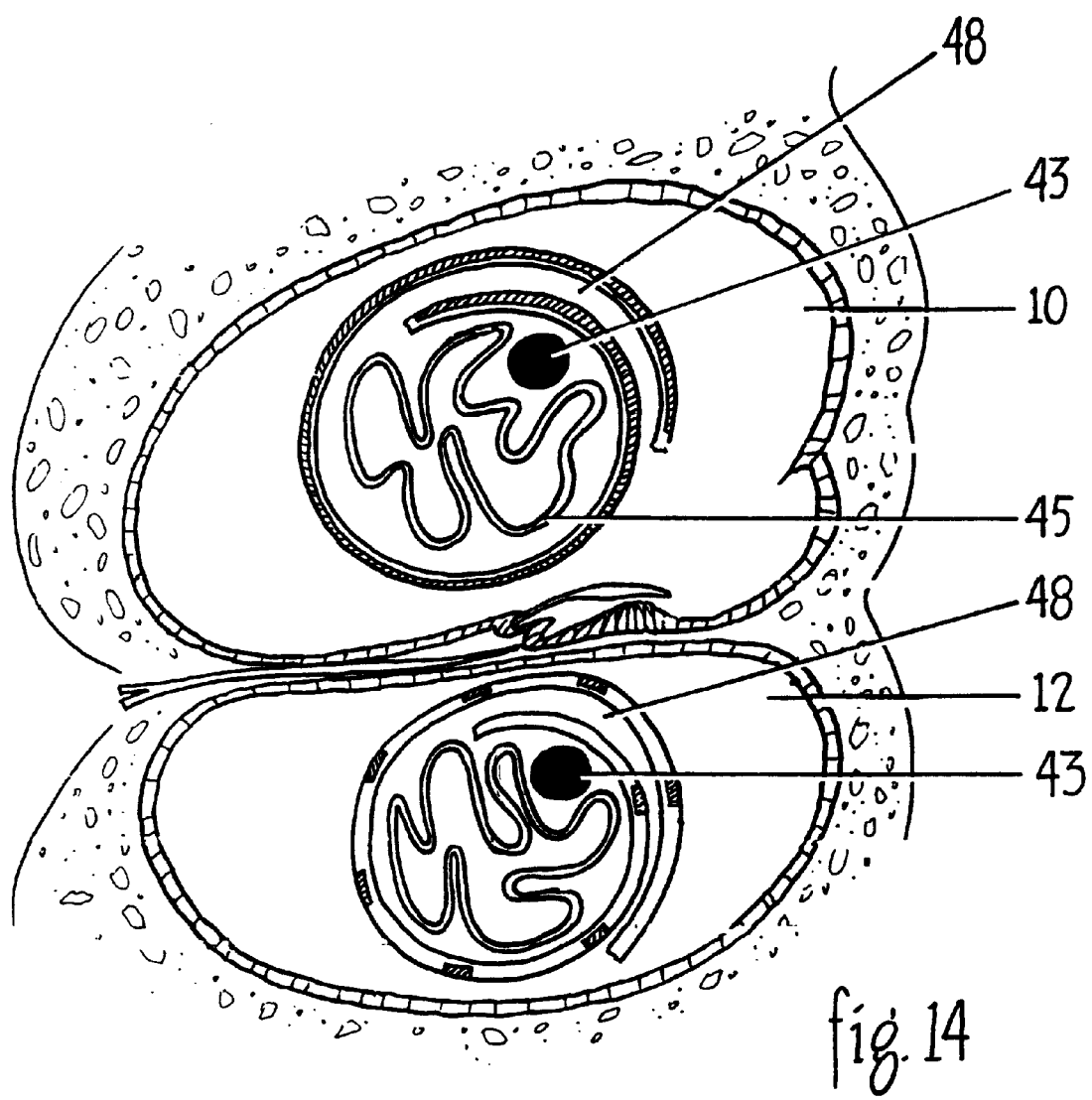
FIG. 14 is a cross sectional view of two scalae of the cochlea with electrode bearing prongs coiled around a catheter-like tube prior to expansion of the prongs.

Means to expand said prongs of the electrode array in situ after insertion into the cochlea can be conveniently accomplished by the surgeon by expanding the catheter-like device 45 present within the coiled-up prongs as shown in the sketch in FIG. 14. The preferred embodiment uses a thin-walled tube 45 that can be inflated by injecting, for example, a saline solution at low pressure. Alternately, one can use other fluids or gases to inflate said catheter-like device to expand one or both prongs in situ. Further, the inside of the catheter-like tube can be filled with a low viscosity fluid such as medical grade silicon, which will subsequently solidify to a relatively soft consistency. It is preferred to inflate both prongs at substantially similar pressures and at substantially the same time, thereby minimiing damaging the thin delicate basilar membrane. This is best achieved if the catheter-like tubes associated with each prong communicate with one another. Such substantially simultaneous equal pressure applied in situ on the coiled-up prongs can be preformed by the surgeon using gentle pressure in both prongs.

Figure 15:
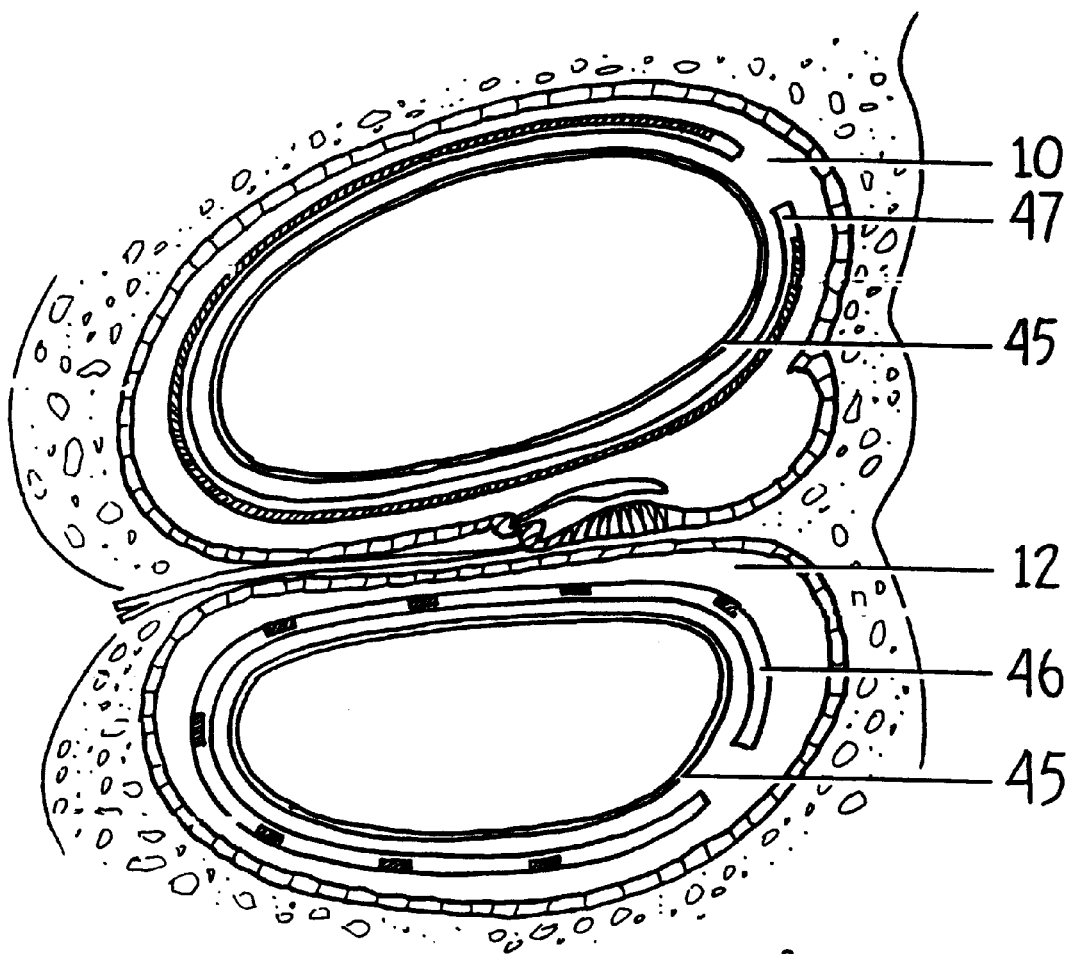
FIG. 15 is a cross sectional view of two scalae of the cochlea with electrode bearing prongs with the catheter-like tube in its expanded state.

Monitoring of pressure with a pressure indicating device 51 during inflation of said prongs allows the surgeon to expand both prongs to substantially touch the walls of the scalae. Upon deflating the catheter-like device, the generally elliptical shape and physical structure of the electrode array positioned in the oval-shaped scalae will tend to retain the expanded shape of the electrode array. The surgeon has the option of leaving the catheter-like device in the expanded prongs, or removing the catheter-like device. FIG. 15 shows the expanded prongs 46, 47 in their respective scala 12, 10 without the catheter-like device. The extent of the overlap of the ends of the rolled-up prongs (48) will vary from patient to patient due to the natural variation in human scala circumferences.

In the case where electrode arrays are implanted in both the scala tympani and the scala vestibuli, Reissner's membrane 49 (FIG. 3), which is very fragile, is considered as if it was a part of the field of the surgical method since the electrode in the scala vestibuli also occupies the scala media 15. In selected cases, where ossification in one of the canals prevents insertion, only one of the electrodes may be inserted in the available scala. Closure and adjustment of the cochlea and scalae includes the possible removal of the catheter-like device, although it is made of biocompatible material and may be left in place. It also includes the injection of normal saline or an electrolyte solution which is as close as possible in content to the perilymph. This is used to displace any air in the scalae. The tunnel(s) is(are) closed with a plug of soft tissue or of bone or bone glue or other glue.

In the preferred embodiment, we have described a transcanal approach through a postauricular incision to both move the annulus aside and to drill the cochlea and insert the electrode array. However, the step of moving the annulus aside may also be accomplished through an endaural or tympanotomy incision made in the interior portion of the external ear canal so as to access the annulus. This approach may then be combined with a postauricular incision approach for drilling the cochlea and inserting the electrode array.

Once the electrode arrays are in place and uncoiled, the inserting materials and tools can then be removed. The electrical conductors embedded in a non-conductive carrier of the implant can be extended from the cochlea to the surface of the temporal bone and, if necessary, laid in a groove in the bony ear canal and extended through the soft tissues to the post-auricular area.

The tympanotomy flap is returned to its original place. Some gelfoam may be placed over the tympanotomy incision. The post-auricular incision is closed with absorbable and/or non-absorbable sutures and a dressing is applied.

One embodiment of the invention is to leave the hole which has been drilled into the cochlea open so as to allow the perilymph fluid to drain into the middle ear on a ongoing basis. This will ensure that there is only minimal (or no) electrical short between the scalae via the helicotrema. The displacement of the perilymph fluid does not appear to be a medical problem (i.e. it is not needed to keep the scalae healthy) and ensures that the electrical conduction is mostly across the basilar membrane and or the spiral ganglion cells near the modiolus, depending on the selection of the pairing of the electrodes between the scalae. A further embodiment is to keep the space inside the scala relatively free of perilymph fluid by inflating the catheter-like tube with a fluid such as silicone, that will harden somewhat to a soft consistency, for example, over a period of 5 to 20 minutes, after which time the catheter-like tube and silicone core is cut at the opening where the catheter-like tube enters the cochlea. This embodiment will also serve to maintain the shape of the expanded prongs against the walls of the scalae and to reduce growth of fibrous tissue around the prongs (which can cause subsequent bone growth in the scalae).

In some patients there may be a broad spectrum antibiotic coverage given for the surgery and in addition, the wound may be irrigated with antibiotics before the opening of the cochlea and after wound closure.

The above description has been intended to illustrate the preferred and alternative embodiments of the invention. It will be appreciated that modifications and adaptations to such embodiments may be practised without departing from the scope of the invention, such scope being most properly defined by reference to this specification as a whole and to the following claims.

What is claimed is:

1. A method of implanting and positioning an electrode array in at least one scala of the cochlea comprising the steps of:
   gaining surgical access the scala via a transcanal approach by moving the annulus aside via a postauricular, endaural or tomyincision made in the interior portion of the exteral ear canal, and then drilling a hole in the basal turn of the cocblea;
   rolling or coiliing said around a catheter-like tube;
   implanting said rolled or coiled up array into a scala by genty pushin said rolled or coiled up array into the hole drilled into said cochlea basal turn; and
   inflating said catheter-like tube in-vivo so as to partly unroll or uncoil said array, thereby positioning the array electrodes in close proximity to the scala walls.

2. A method according to claim 1, wherein:
   the electrode array comprises two prongs, one of said prongs being rolled or coiled around a first catheter-like tube, and the other of said prongs is rolled or coiled around a second catheter-like tube;
   one of said rolled or coiled up prongs is inserted into a first scala and the other of said rolled or coiled prong up is inserted into a second scala; and each of said catheter-like tubes is inflated after insertion.

3. A method according to claim 1, wherein said step of inflating the catheter-like tube is accomplished by introducing a fluid or gas into said catheter-like tube.

4. A method according to claim 3 wherein said fluid or gas is introduced under pressure.

5. A method according to claim 2, wherein the step of inflating the catheter-like tubes is accomplished by introducing a fluid or gas under pressure into each of said catheter-like tubes, and wherein the catheter-like tubes associated with the two prongs are connected to one another and equal pressure is applied to both tubes simultaneously so as to minimize pressure differences between the two scalae, thereby minizing damage to the delicate basalar membrane.

6. A method according to claim 4, further comprising the step of deflating the catheter-like tube.

7. A method according to claim 6 further comprising the step of removing the tube.

8. A method according to claim 6 further comprising the step of cutting the tube at the window leading into the scala and leaving the intracochlear portion of the tube in the cochlea.

9. A method according to claim 4 wherein hyaluronidase is used to lubricate the electrodes prior to implantation.

10. A method according to claim 3 wherein a fluid is used to inflate the catheter-like tube, said fluid being adapted to harden somewhat to a soft consistency, and further including the steps of allowing said fluid to harden to a soft consistency and cutting the catheter-like tube and silicone core where it enters the cochlea.

* * * * *

UNITED STATES PATENT AND TRADEMARK OFFICE
CERTIFICATE OF CORRECTION

PATENT NO. : 6,306,168 B1
DATED : October 23, 2001
INVENTOR(S) : Peter Berrang and Alan Lupin It is certified that error appears in the above-identified patent and that said Letters Patent is hereby corrected as shown below:

Column 10,
Line 47, the portion reading "access the scala" should read -- access to the scala --.
Line 49, the portion reading "tomyincision" should read -- tympanotomy incision --.
Line 51, the portion reading "cocblea" should read -- cochlea --.
Line 52, the portion reading "coiliing said around" should read -- coiling said array around --.
Line 54, the portion reading "genty pushin" should read -- gently pushing --.
Line 66, the portion reading "coiled prong up" should read -- coiled up prong --.

Column 11,
Line 15, the portion reading "minizing" should read -- minimizing --.

Signed and Sealed this

Ninth Day of April, 2002

JAMES E. ROGAN
Director of the United States Patent and Trademark Office